US006214056B1

(12) United States Patent
Wilkinson

(10) Patent No.: US 6,214,056 B1
(45) Date of Patent: Apr. 10, 2001

(54) SHOCK ABSORBER PROSTHETIC APPARATUS

(76) Inventor: Kerry E. Wilkinson, 5750 West Linda La., Chandler, AZ (US) 85226

( * ) Notice: Subject to any disclaimer, the term of this patent is extended or adjusted under 35 U.S.C. 154(b) by 0 days.

(21) Appl. No.: 09/389,735

(22) Filed: Sep. 7, 1999

(51) Int. Cl.[7] .................................................. A61F 2/62
(52) U.S. Cl. ................................................................ 623/35
(58) Field of Search ............................... 623/27, 32, 33, 623/34, 35, 38

(56) References Cited

U.S. PATENT DOCUMENTS

| 4,038,705 | * | 8/1977 | Owens et al. .......................... 623/35 |
| 4,134,159 | * | 1/1979 | Wilson ................................... 623/27 |
| 5,800,451 | | 9/1998 | Wilkinson . |
| 5,800,563 | * | 9/1998 | Arbogast et al. ...................... 623/35 |
| 5,888,214 | | 3/1999 | Ochoa . |
| 5,961,556 | * | 10/1999 | Thorn ..................................... 623/27 |
| 5,984,972 | * | 11/1999 | Huston et al. ......................... 623/35 |

\* cited by examiner

*Primary Examiner*—Bruce Snow
(74) *Attorney, Agent, or Firm*—H. Gordon Shields

(57) ABSTRACT

Shock absorber apparatus for a prosthetic leg and foot includes an elastomeric element secured to a pair of sleeves. The elastomeric element is secured to the sleeves through end retainers which are secured to the elastomeric element. The elastomeric element provides both shock absorber and torsional resistance functions. A cable, or a plurality of cables, is/are disposed about the elastomeric element and the end retainers to provide additional torsional resistance for the shock absorber apparatus. The shock absorber apparatus is appropriately secured to a prosthetic foot and to a user's leg or knee by conventional elements.

2 Claims, 1 Drawing Sheet

SHOCK ABSORBER PROSTHETIC APPARATUS

BACKGROUND OF THE INVENTION

1. Field of the Invention

This invention relates to a shock absorber apparatus, and, more particularly, to a shock absorber apparatus for a prosthetic leg.

2. Description of the Prior Art

Two problems with prosthetic legs in general are the inability to absorb shocks and to rotate. Shock absorption increases the natural feel and comfort of the leg. Rotation to some degree allows a more ordinary turn while walking or even the pivot action required for golf baseball, etc.

U.S. Pat. No. 5,800,562 (Wilkinson), the inventor of which is the inventor of the present apparatus, discloses shock absorber apparatus for a prosthetic leg which utilizes a pair of cylindrical sleeves and elastomeric elements disposed within the sleeves for absorbing shocks. A spring element within the elastomeric elements allows limited rotational movement.

U.S. Pat. No. 5,888,214 (Ochoa) discloses the use of an elastomeric element as a shock absorber in a prosthetic leg. Tile apparatus is adjustable.

The apparatus of the present invention comprises a shock absorber which is efficient and light weight and provides a degree of rotational flexibility. The apparatus is made to interface with industry standard components and to fit anywhere between the foot and an upper socket or socket connector, as appropriate or as desired. The apparatus utilizes a single elastomeric element which provides tension, and compression absorbing characteristics and rotational resistance.

SUMMARY OF THE INVENTION

The invention claimed and described herein comprises a shock absorber apparatus for a prosthetic leg. The apparatus includes a single elastomeric element secured to a pair of retainer elements. The retainer elements are in turn secured to a pair of cylindrical elements for relative movement. The elastomeric element has a square cross sectional configuration for maximum surface area for attachment to the end retainer elements. Threads or cables are secured to the end retainers and are disposed about the elastomeric element for additional torsional resistance.

Among the objects of the present invention are the following:

To provide new and useful prosthetic apparatus;

To provide new and useful prosthetic shock absorber apparatus;

To provide new and useful prosthetic apparatus with rotational capabilities;

To provide new and useful prosthetic shock absorber assembly having an elastomeric element secured to a pair of end retainers and relative rotation between the two; and To provide new and useful shock absorber elements including an elastomeric element secured to retainer elements and disposed between a pair of cylindrical elements.

DESCRIPTION OF THE PREFERRED EMBODIMENT

Figure 1:
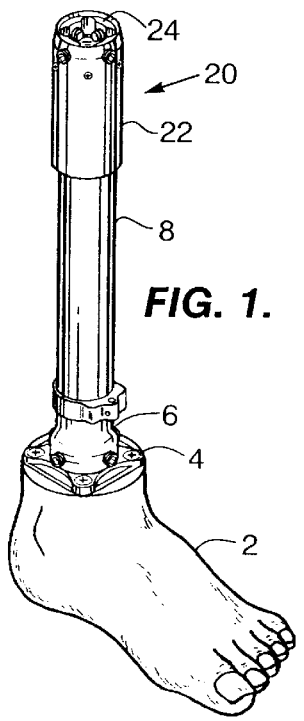
FIG. 1 is a perspective view of the apparatus of the present invention in the use environment secured to a prosthetic foot.
Figure 2:
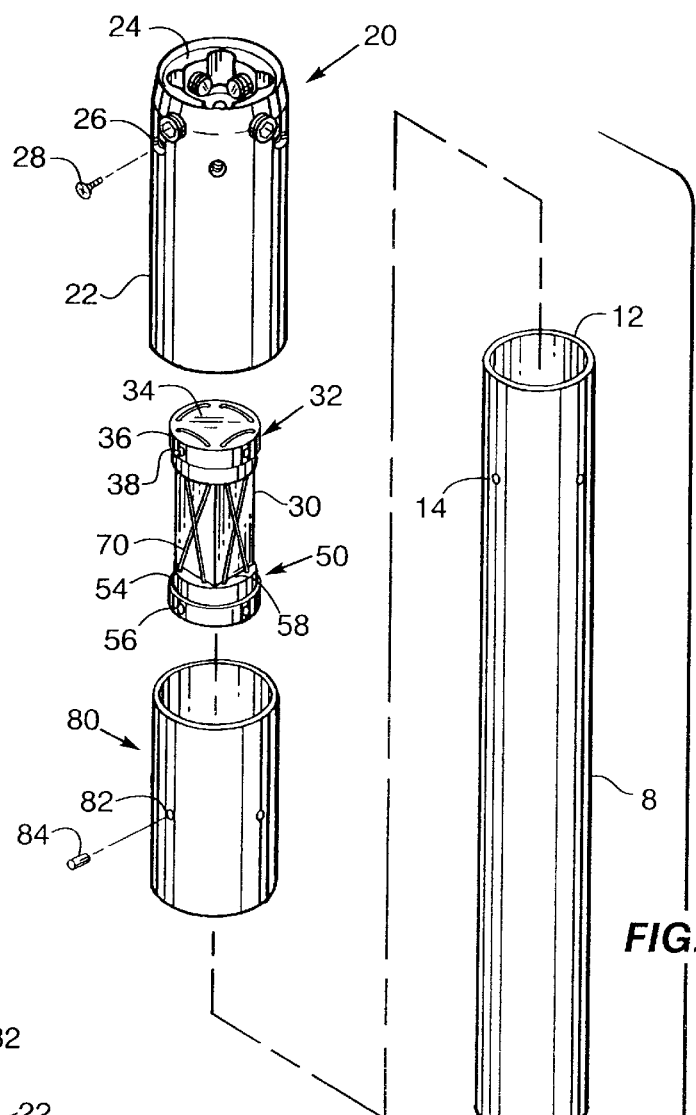
FIG. 2 is an exploded perspective view of the apparatus of the present invention.
Figure 3:
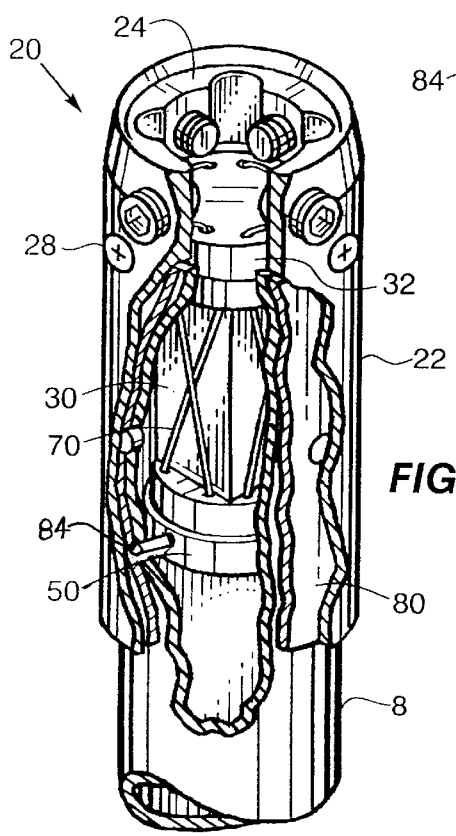
FIG. 3 is a perspective view partially broken away of the apparatus of the present invention.

FIG. 1 is a perspective view of prosthetic foot 2 to which is secured shock absorber apparatus 20 embodying the present invention. FIG. 2 is an exploded perspective view of the apparatus of FIG. 1, except that the foot 2 is not shown. The foot 2 comprises the use environment of the apparatus 20. FIG. 3 is a view in partial section, or partially broken away, of the apparatus of the present invention. The apparatus 20 is shown with the various elements assembled together. Portions of the elements are broken away for convenience of illustration. For the following discussion, reference will be made to all three Figures.

A conventional base connector 4 is secured to the foot 2. A conventional sleeve connector 6 is in turn secured to the base connector 4. Extending upwardly from the sleeve connector 6 is a tube 8. The tube 8 includes a bottom end 10, an upper or top end 12, and spaced apart apertures 14 adjacent to the upper end 12. The apertures 14 are spaced downwardly from the top 12. The bottom end 10 of the sleeve 8 extends into the sleeve connector 6 to secure the tube 8 to the foot 2.

Shock absorber apparatus 20 includes an outer cylindrical sleeve 22, an elastomeric element 30 secured thereto, and a lower sleeve 80 which is also secured to the elastomeric element 30.

The outer cylindrical sleeve 22 includes conventional connector elements 24 adjacent to the top of the sleeve 22. The connector elements 24 mate with a base connector element, such as the base connector element 4, which, in this situation is illustrated in FIG. 1, would be secured to the knee of a user of the apparatus. Such elements are well known and understood in the art.

The sleeve 22 includes a plurality of spaced apart apertures 26 and a screw 28 is shown adjacent to one of the apertures 26. Screws, like the screw 28, extend through the apertures 26 and into tabbed apertures 38 in an upper end retainer 32. The upper end retainer 32 includes a top 34 and a cylindrical portion 36 extending downwardly from the top 34. The tabbed apertures extend through the cylindrical portion 36.

The end retainer 32 also includes a square socket which receives one end of the elastomeric element 30. The elastomeric element 30 has a square cross sectional configuration to provide maximum surface area for connecting to both the upper end retainer 32 and a lower end retainer 50. The elastomeric element 30 provides both shock absorber and torsional resistance functions.

The lower end retainer 50 is similar to the upper end retainer 32. It includes a cylindrical portion 53, and apertures 56 extend through the cylindrical portion 54. A base 58 is shown at the upper end of the cylindrical portion 54. The base 58 includes a square aperture which receives the bottom of the elastomeric element 30.

A cable 70 is shown disposed on the exterior of the elastomeric element 30. The cable 70 extends upwardly through the upper end retainer 30, through apertures in the top 34, and then downwardly through appropriate apertures in the lower end retainer 50. As illustrated, the sides of the elastomeric element 30 have an "X" configuration in the cable. The purpose of the cable 70 is to provide additional torsional resistance for the elastomeric element 30. The cable ends are, of course, appropriately secured together or appropriately secured to either the top 34 of the upper end retainer element 32 or the bottom (not shown) of the lower end retainer 50. Another purpose of the cable 70 is to provide a safety function. Thus, if the elastomeric element 30 were to fail, the cable 70 would prevent the overall failure of the apparatus 20.

The cable may be appropriately sized, as desired, and may have any appropriate winding configuration on the size of the elastomeric element 30. The shock absorber apparatus 20, and its various components, will, of course, be designed appropriately with the size and weight and expected activity of a user of the apparatus.

The lower sleeve 80 is of general cylindrical configuration with a plurality of apertures 82 extending through the sleeve. Pins, such as a pin 84, extend through the apertures 82 and into the apertures 56 of the lower end retainer. The pins 84 also extend through the apertures 14 in the tube 8. The tube 8 is disposed between the sleeve 80 and the elastomeric element 30 to secure the shock absorber apparatus 20 to the tube 8 and thus to the foot 2.

It is obvious that the sleeve 80 may be connected directly to the sleeve connector 6, if desired, as where the apparatus is in a relatively short installation. Or, in the alternative, the sleeve connector 6 may be secured directly to the bottom retainer 50 where length is a concern.

The lower sleeve 80, in the embodiment of FIGS. 2 and 3, is secured directly to the tube 8 and also to the lower end retainer 50 of the elastomeric element 30 by the pins 84.

The upper end retainer 32 of the elastomeric element 30 is secured to the outer cylinder sleeve 22 by screws 28 which extend thru the apertures 26 in the sleeve 22 and into the apertures 38 in the elastomeric element 30.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, within the limits only of the true spirit and scope of the invention.

What I claim is:

1. Prosthetic shock absorber apparatus comprising in combination:

a first sleeve;

a second sleeve;

elastomeric means secured to the first and second sleeves for absorbing shocks and for providing tortional resistance, including a cable extending about the elastomeric element and between the first and second retainers to provide additional torsional resistance; and means for securing the first and second sleeves to a prosthetic foot.

2. Prosthetic shock absorber apparatus comprising in combination:

a first sleeve;

a second sleeve;

elastomeric means secured to the first and second sleeves for absorbing shocks, including an elastomeric element having a first end and a second end, a first retainer secured to the first end, a second retainer secured to the second end, and a cable extending about the elastomeric element and between the first and second retainers to provide torsional resistance; and means for securing the first and second sleeves to a prosthetic foot.

* * * * *